(12) United States Patent
Reissmann

(10) Patent No.: US 8,025,059 B2
(45) Date of Patent: Sep. 27, 2011

(54) RESPIRATORY DEVICE COMPRISING A DOUBLE LUMEN ENDOTRACHEAL TUBE

(75) Inventor: Hajo Reissmann, Hamburg (DE)

(73) Assignee: Hajo Reissman, Hamburg (DE)

( * ) Notice: Subject to any disclaimer, the term of this patent is extended or adjusted under 35 U.S.C. 154(b) by 1061 days.

(21) Appl. No.: 10/555,142

(22) PCT Filed: Apr. 15, 2004

(86) PCT No.: PCT/EP2004/003935
§ 371 (c)(1),
(2), (4) Date: Jun. 4, 2008

(87) PCT Pub. No.: WO2004/096312
PCT Pub. Date: Nov. 11, 2004

(65) Prior Publication Data
US 2008/0236590 A1    Oct. 2, 2008

(30) Foreign Application Priority Data
Apr. 30, 2003    (DE) .................................. 103 19 384

(51) Int. Cl.
*A61M 16/00*    (2006.01)
*A62B 9/06*    (2006.01)

(52) U.S. Cl. ......... 128/207.14; 128/207.18; 128/200.24; 128/911; 128/912

(58) Field of Classification Search ............. 128/207.14, 128/207.15, 200.26, 207.16–207.18, 200.24, 128/200.28, 206.26, 911–912; 600/435, 600/466, 531; 604/508, 96.01, 103.04, 43, 604/105, 106, 93.01, 98.01, 102.01, 118–119, 604/128

See application file for complete search history.

(56) References Cited

U.S. PATENT DOCUMENTS

| | | | |
|---|---|---|---|
| 2,318,518 A | 5/1943 | Opperer | |
| 3,102,537 A | 9/1963 | Bartlett, Jr. | |
| 3,871,373 A | 3/1975 | Jackson | |
| 3,912,795 A | 10/1975 | Jackson | |
| 4,048,993 A | 9/1977 | Dobritz | |
| 5,040,532 A | 8/1991 | Alfery | |
| 5,059,170 A * | 10/1991 | Cameron | 604/43 |
| 5,207,220 A | 5/1993 | Long | |
| 5,309,906 A * | 5/1994 | LaBombard | 128/207.14 |
| 5,372,131 A | 12/1994 | Heinen, Jr. | |
| 5,499,625 A * | 3/1996 | Frass et al. | 128/207.15 |
| 5,582,167 A | 12/1996 | Joseph | |
| 5,706,830 A | 1/1998 | Parker | |
| 5,740,796 A | 4/1998 | Skog | |

(Continued)

FOREIGN PATENT DOCUMENTS
DE    25 35 191    2/1977
(Continued)

*Primary Examiner* — Justine Yu
*Assistant Examiner* — Colin W Stuart
(74) *Attorney, Agent, or Firm* — Womble Carlyle Sandridge & Rice, PLLC

(57) ABSTRACT

Device for ventilation with a double lumen endotracheal tube featuring a connecting piece at the end distal to the patient into which the two lumina of the endotracheal tube are extended, separated within the connecting piece by an axial partition wall, a connector with two nozzles leading to a joint connecting section and separated from each other by another partition wall, the connector being attachable to the connecting piece in a way that brings the partition wall and the other partition wall into a sealing contact, a ventilator and at least one tube connected to a nozzle of the connector at one end and to the ventilator at the other.

36 Claims, 3 Drawing Sheets

U.S. PATENT DOCUMENTS

Figure 1:
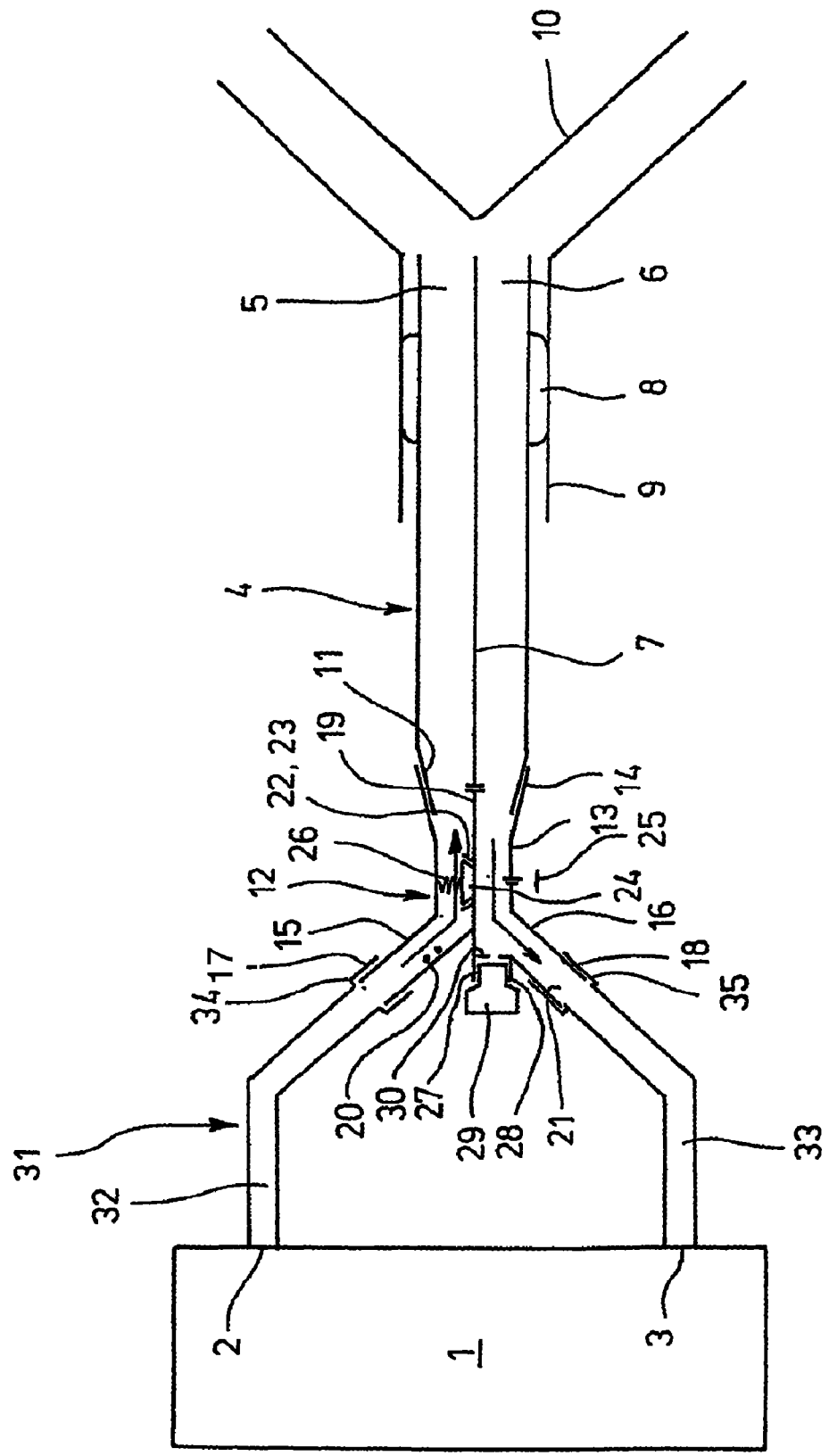

| | | | |
|---|---|---|---|
| 6,166,092 | A | 12/2000 | Sekins et al. |
| 6,272,933 | B1 | 8/2001 | Gradon et al. |
| 6,390,092 | B1 | 5/2002 | Leenhoven |
| 6,390,988 | B1 | 5/2002 | Robinson |
| 6,502,572 | B1 | 1/2003 | Berthon-Jones et al. |
| 6,510,841 | B1 | 1/2003 | Stier |
| 6,533,730 | B2 | 3/2003 | Strom |
| 6,598,602 | B1 | 7/2003 | Sjoholm |
| 6,626,169 | B2 | 9/2003 | Gaitini |
| 6,840,241 | B2 | 1/2005 | Strom |
| 2002/0148464 | A1 * | 10/2002 | Hoenig ............ 128/200.24 |

FOREIGN PATENT DOCUMENTS

| | | |
|---|---|---|
| DE | 195 28 113 | 2/1997 |
| EP | 0 806 218 | 11/1997 |
| WO | WO 02/089885 A2 | 11/2002 |

* cited by examiner (a)

(b)

RESPIRATORY DEVICE COMPRISING A DOUBLE LUMEN ENDOTRACHEAL TUBE

The invention relates to a device for ventilation via a double lumen endotracheal tube.

The majority of patients being ventilated for intensive care or anesthesia has their airway secured by an endotracheal tube. The latter usually is made from rubber or plastic. It is inserted either through the natural upper airways, i.e. mouth or nose, pharynx, and larynx, or by surgical access to the trachea, i.e. tracheostomy. Generally, the endotracheal tube is equipped with an inflatable cuff around its tracheal end, which seals the trachea and thus allows positive pressure ventilation and protects the airway from contamination by foreign matter. The end of the tube distal to the patient is either coupled to a ventilator via a tubing system or open to ambient air via a check valve at its outlet.

Common single lumen endotracheal tubes are equipped with a standardized joining piece, a nearly cylindrical cone approximately 10 mm long with an outer diameter of 15 mm. The inspiratory and expiratory tubes are joined in a Y-connector, which offers a corresponding female cone into which the joining piece of the endotracheal tube can be inserted, forming an airtight connection.

With double lumen endotracheal tubes, as described in WO 02/089885 A, usually each lumen is connected via its own standardized joining piece and a straight connector with corresponding female cone to the inspiratory and the expiratory tube, respectively.

This type of connection, however, is impractical and poses safety hazards: Two connectors double the risk of disconnection. Furthermore, two pairs of joining pieces and connectors of identical dimensions may lead to confusion of the two lumina. Color coding or similar marks offer merely limited protection in this respect. A connection with a ventilator using a conventional Y-connector is not readily feasible.

In case of a malfunction jeopardizing regular delivery of gas to the patient, conventional ventilators in connection with single lumen endotracheal tubes open a safety valve in their inspiratory limb, at least allowing the patient to breathe ambient air, if he is physically able. The expiratory valve usually allows expiration in this case of malfunction, and both valves cooperate to secure the necessary unidirectional flow of air. With a double lumen endotracheal tube, one lumen each is available for inspiration and expiration, respectively, also in this case of malfunction. The patient would be confronted with relatively high flow resistances, especially if the double lumen endotracheal tube would feature an asymmetrical design with a narrower inspiratory lumen, which from the standpoint of regular ventilation is the preferred design.

Accordingly the invention is based on the task to create a device allowing ventilation via a safe and easy to operate connection between a double lumen endotracheal tube and a ventilator.

This problem is solved by a device for ventilation having the features stated in claim 1. Advantageous embodiments of the device are described in the adjacent claims.

A device for ventilation constructed according to the inventions is comprised of
1. a double lumen endotracheal tube with a joining piece at the end distal to the patient, into which the two lumina of the endotracheal tube are inserted, being separated by an axial partition wall within the joining piece,
2. a connector with two openings for ventilator tubing leading to an opening accepting the above mentioned joining piece, another axial partition wall within the connector forming a continuous sealing partition together with the partition wall of the joining piece when the latter is inserted into the connector,
3. a ventilator and
4. at least one tube leading from the ventilator to one of the openings of the connector.

A device according to the invention allows to separately connect the two lumina of the endotracheal tube to the two limbs of a ventilator tubing system or to an inspiratory tube and an expiratory valve leading into the atmosphere via a suitable connector. For this purpose the two lumina are continued into the joining piece and separated therein by an axial partition wall, likewise the tubing system limbs are continued towards the opening within the connector accepting the joining piece and separated by another axial partition wall. Furthermore, when the joining piece is introduced into the connector the partition wall will come into sealing contact with the other partition wall, securing a separation of inspiratory and expiratory airways throughout ventilator tubing and endotracheal tube. With only one connection between endotracheal tube and ventilator handling is easier and the risk of an inadvertent disconnection is reduced. In principle the double lumen endotracheal tube can be connected to ventilator through a conventional Y-connector, e.g. in case a ventilator with a connector described in this invention is not available.

According to one embodiment the joining piece has a circular external circumference and the opening accepting it a corresponding circular internal circumference, like in the standardized Y-connectors. According to another embodiment the joining piece and the accepting opening are conical or cylindrical.

According to one embodiment the connector is Y-shaped, as conventional connectors, or T-shaped. In principle it is possible to construct the connector from a conventional Y-connector and an adapter introduced into its cone which incorporates the other partition wall and a cone of its own accepting the joining piece.

The seal between the partition wall and the other partition wall can be obtained in several ways. For this purpose according to one embodiment the walls meet bluntly or overlap partially. According to another embodiment soft elastic seals become effective between the walls.

The partition walls can have various cross sections. According to one embodiment the partition walls are shaped like plates or tubes. A conical or cylindrical joining piece and a conical or cylindrical connector opening are partitioned into lumina with circle segment cross sections by plate-shaped partition walls. Tube-shaped partition walls are preferably located in a concentric position within the joining piece and the connector opening.

According to one embodiment the joining piece has an external diameter of approximately 15 mm, the connector opening having a corresponding internal diameter. According to another embodiment the joining piece has an internal diameter of approximately 22 mm and the connector opening an external diameter of approximately 22 mm. These embodiments allow the double lumen endotracheal tube to be used with conventional connectors at the ventilator tubing and the connector to be used with conventional single lumen endotracheal tubes or ventilation masks. They make use of the fact that there are two standards for the connection of tubing, Y-connectors, etc. to endotracheal tubes, ventilation masks etc.:

5. 15 mm, female at the side of the ventilator (breathing bag, . . . ), male towards the patient—usually but not exclusively used for endotracheal tubes,
6. 22 mm, male at the side of the ventilator (breathing bag, . . . ), female towards the patient—usually but not exclusively used for ventilation masks.

According to one embodiment a tube-shaped partition wall in the joining piece has an external diameter of approximately 15 mm, and the other partition wall in the connector opening is tube-shaped with an internal diameter of approximately 15 mm, the entire joining piece has an internal diameter of approximately 22 mm and the connector opening an external diameter of approximately 22 mm. In this way the patient side (at the double lumen endotracheal tube) has both a 15 mm male and a 22 mm female part; towards the ventilator (breathing bag, . . . ), i.e. there is the connector with a 15 mm female as well as a 22 mm male part. The latter in this respect resembles conventional connectors, several of which have an opening complying with both standards (i.e. forming a nozzle of 15 mm internal diameter and 22 mm external diameter) in order to flexibly function together with a variety of endotracheal tubes, ventilation masks etc. According to the invention both standards can be applied at the same time for separately connecting the two lumina of the endotracheal tube to the two limbs of the tubing via the lumen within the tube-shaped partition walls and the ring-shaped lumen around the partition walls, respectively. Although not necessary, using the interior lumen with its full cross section for expiration is advantageous, since it allows unimpeded passage of a suction catheter. In this case inspiration would take place through the ring-shaped exterior lumen. An additional advantage of such solution is the rotational symmetry allowing connection in arbitrary rotational positions.

Such connector can be used with conventional single lumen endotracheal tubes, if a valve of suitable construction makes sure that the circular lumen is blocked and a shortcut between the two lumina is opened. Furthermore the joining piece can be used with a conventional Y-connector. If both lumina of the endotracheal tube are to be used, a shortcut between the two lumina has to be provided, e.g. by a valve. This is, however, not urgently necessary, because, in the preferred embodiment, the central lumen of the joining piece is continued into the wider one of two unequally wide endotracheal tube lumina.

According to one embodiment the joining piece has at least one groove and the connector at least one complementary projection or vice versa, which articulate when the joining piece is inserted into the connector. By their arrangement they allow a connection only in a defined rotational orientation, thus ensuring a correct connection of the endotracheal tube lumina with the inspiratory and expiratory limb of the ventilator tubing, respectively. In principle the correct connection can also be secured by plate-shaped partition walls overlapping each other and being situated excentrically within joining piece and connector. Furthermore this is secured by partition walls forming concentric circular tubes; these would allow arbitrary rotational positions.

According to one embodiment the connector and/or the joining piece contain a shutter bridging the two sides of the partition wall or the other partition wall. This shutter can be opened in case of ventilator malfunction in order to allow spontaneous breathing via both lumina of the endotracheal tube. This makes sure that a spontaneously breathing patient is not confronted with unduly high resistances, especially if the double lumen endotracheal tube is asymmetrical by design.

In addition, connecting the two tubing limbs by opening the shutter is advantageous for the following reasons: In case of a leakage somewhere between ventilator and patient, a ventilator in a pressure-regulated mode of ventilation tries to restitute the set pressure by increasing gas delivery up to the technically feasible maximum. In case of large leaks, e.g. a disconnection, this usually will not be successful. In case of a disconnection within the expiratory limb during ventilation through a double lumen endotracheal tube, the compensatory delivery of gas is directed through the endotracheal tube, i.e. through the trachea. Depending on the resistance of the expiratory limb of the endotracheal tube and the parts between endotracheal tube and the site of disconnection unwanted high pressures might ensue. In this case of malfunction a shortcut between the tubing limbs is useful.

According to one embodiment the closing element of the shutter has its seat in the partition wall and/or the other partition wall. By moving the closing element away from its seat the partitioning wall is opened. The closing element can e.g. be a valve cone or a flap.

According to one embodiment the shutter can be operated manually from the outside by a suitable actuator. The manual operation can be performed by the medical personnel. According to one embodiment the shutter has an operating connection with a control component of the ventilator. Operation of the shutter by the ventilator can be implemented with a high degree of reliability. According to one embodiment the shutter has an operating connection with a pressure sensor in the expiratory or inspiratory limb, e.g. within the ventilator tubing. Under normal conditions the pressure at these sites is more or less positive. Negative pressures mean a malfunction. This solution avoids the unreliable operation by band as well as modifications to the ventilator. In principle the various alternatives for operating the shutter can be freely combined.

According to one embodiment the shutter has a mark which is visible from the outside and shows at all times, whether the two lumina of the double lumen endotracheal tube are used separately in their respective phases, i.e. as intended, or simultaneously. According to one embodiment the shutter has a sensor for the position of the closing element connected to the control component of the ventilator. This way the status of the shutter can automatically be taken into account during regulation of ventilation and/or display of operating data and/or alarm conditions.

According to one embodiment the connector features joints for the tubing which can be swiveled around at lest one axis. This allows the tubes to approach the connector from a wide range of angles. Rotating or swiveling joints with one or more axes or ball joints are conceivable.

According to one embodiment the connector is equipped with a closable opening which, when opened, allows the insertion of a suction catheter into the expiratory lumen of the endotracheal tube. Due to the uninterrupted connection the suction catheter can be inserted into the expiratory lumen of the double lumen endotracheal tube during ongoing ventilation. According to a simple embodiment the device is equipped with a fastener which can seal the opening. In another embodiment the opening is spanned by an perforated elastic membrane, through which the suction catheter can be introduced without producing a leak, so the desired positive pressure in the lungs can be maintained. The perforated elastic membrane is able to adapt to catheters of various diameters.

Subsequently the invention is illustrated using the accompanying drawings of embodiment examples. The drawings show:

FIG. 1 a device for ventilation in a schematic view;

FIGS. 2*a* and *b* the connection between tubing system and ETT of said device in an enlarged partial longitudinal section (FIG. 2*a*) and in a cross section through the connecting region (FIG. 2*b*);

FIGS. 3*a* and *b* an alternative connection between tubing system and ETT in a partial longitudinal section (FIG. 3*a*) and in a cross section through the connecting region (FIG. 3*b*);

FIGS. 4a and b an alternative connection between tubing system and ETT in a partial longitudinal section (FIG. 4a) and in a cross section through the connecting region FIG. 4b);

FIGS. 5a and b an alternative connection between tubing system and ETT in a partial longitudinal section (FIG. 5a) and in a cross section through the connecting region (FIG. 5b).

According to FIG. 1 the device for ventilation comprises of a ventilator 1 with an outlet 2, at which a stream of gas is provided for ventilation. Furthermore, the ventilator 1 has an inlet 3, to which a stream of exhaled gas can be conducted.

At the inlet 3 the ventilator 1 has an active valve, which is closed during inspiration in order to preserve the pressure in the lungs, and which is opened for expiration. Behind the valve the expired gas can be released into the surroundings. Alternatively the expired stream of gas can be reconditioned within the ventilator 1 ($CO_2$) and the gas needed for ventilation can be channeled back to the outlet 2, potentially adding fresh gas for ventilation.

Furthermore, there is an endotracheal tube 4 featuring in an tube-like body two lumina 5, 6, which are separated from each other by an axial wall 7. At its tracheal end this double lumen ETT 4 features an inflatable cuff 8 providing a seal toward the trachea 9 when the ETT 4 is advanced to shortly before the bronchi 10.

At the end distal to the patient the ETT 4 features a joining piece 11 in form of a cone. The partition wall 7 of the ETT is extended into the joining piece 11, ending at approximately half the height of the cone. Furthermore, there is a Y-shaped connector 12. It has in an essentially tubular connecting section 13 a conical opening 14, which is attached to the connecting piece 11 forming a seal.

The connecting section 13 features two separate tube nozzles 15, 16 with tubing connectors 17, 18 at their ends. Furthermore, the connector 12 has another partition wall 19, axially extending approximately from the middle of the conical opening 14 to the intersection of the two nozzles 15, 16. By this the connector 12 is separated into two chambers, one of which 20 extends from the inlet connector 17 into the opening 14, the other extending from the opening 14 towards the outlet connector 18.

Within the other partition wall 19 there is a shutter 22 with a valve seat 23 and a conical valve 24. It can be opened against the force of a spring 26 by a lever 25 extended to the outside.

The outlet chamber 21 features a tube 27 between the nozzles 15, 16, the axis of which is oriented towards the tubular connecting section 13, and which has an opening 28. The opening 28 is closed by a fastener 29. Beneath this fastener the tube 27 features an elastic perforated membrane.

The ventilator 1 is connected to the ETT 4 via a tubing system 31 and the connector 12. The tubing system 31 features an inspiratory tube 32 connecting the ventilator outlet 2 with the connector 17. Thereby the ventilator outlet 2 is connected to the inspiratory lumen 5 of the ETT 4. Furthermore, the tubing system 31 features an expiratory tube 33 connected to the connector 18. In the example the connections 34, of the tubes 32, 33 with the connectors 17, 18 can be freely rotated around the axes of the nozzles 15, 16.

Figure 2:
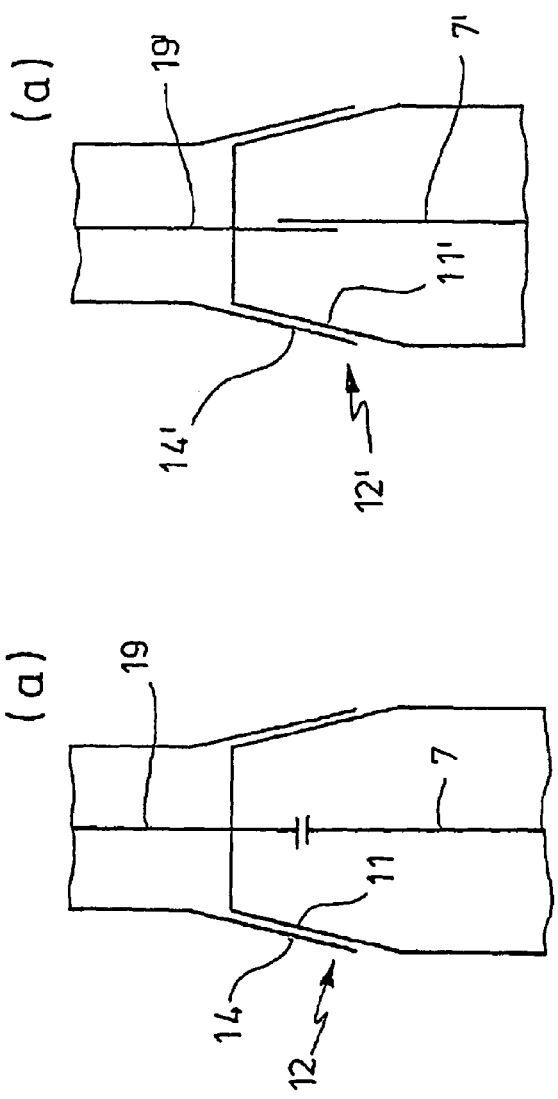

FIG. 2 shows the partition wall and the other partition wall extending diagonally through the connecting piece and the opening 14. When the connecting piece 11 is introduced into the opening 14 forming a seal, the partitioning walls meet bluntly and form a seal, as well. A sealing connection between connecting piece 11 and opening 14 is only feasible in one rotational position, which is defined by an axial groove in the outside of the connecting piece 11 and an axial projection at the inside of the opening 14. Thereby the connections of chamber 20 with lumen 5 and chamber 21 with lumen 6 is guaranteed at all times.

In this way the ventilator 1 can be connected to the ETT 4 by merely sticking the single connector 12 onto the connecting piece 11. The connections of outlet 2 to the inspiratory lumen 5 and the inlet 3 to the expiratory lumen 6, which have different cross sections, is secured. If necessary a conventional Y-connector can be connected to the ETT 4, as well.

After removing the fastener 29 a suction catheter can be introduced into the expiratory lumen 6 down towards the bronchi 10, the perforated membrane 30 around it preserving the seal.

Figure 3:
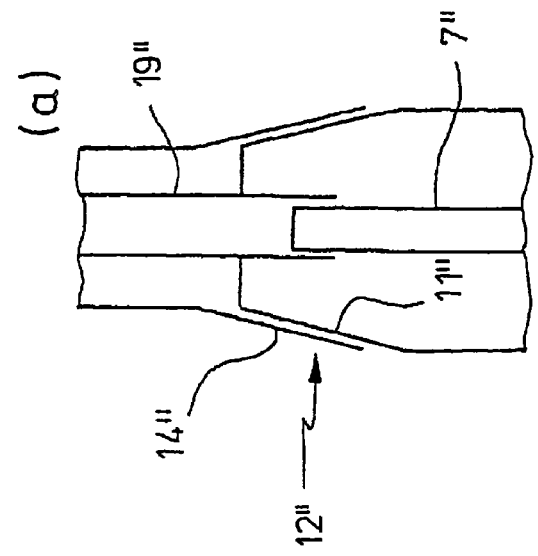

The embodiment in FIG. 3 differs from the one described above by the partition wall 7' and the other partition wall 19' being positioned slightly off the center and forming a seal in a side by side position when the opening 14 is stuck to the connecting piece 11. This arrangement at the same time makes sure that the connector 12' and the connecting piece 11 can only be joined with a defined orientation.

Figure 4:
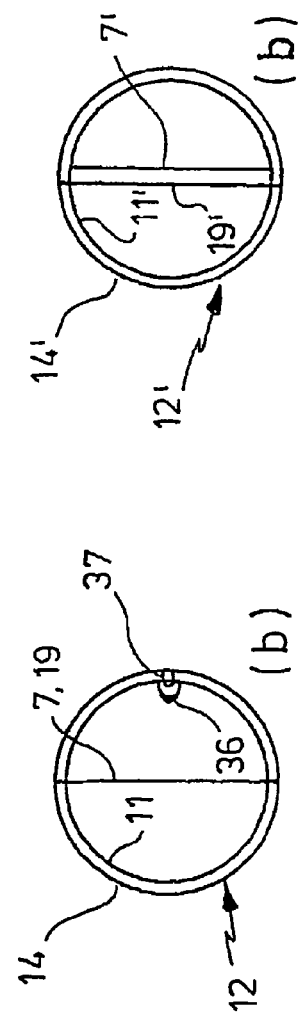

The embodiment in FIG. 4 differs from the ones described above by the partition wall 7" and the other partition wall 19" each being constructed as axially oriented tubes. Preferably the tube 7" is connected to the inspiratory lumen 5 and the tube 19" to the connector 17. The surrounding ring-shaped spaces of the connecting piece 11 and the opening 14 are connected to the expiratory lumen 6 and the connector 18, respectively. Connectors 12" and connecting pieces 11" constructed in this way can be joined in arbitrary rotational orientation.

Figure 5:
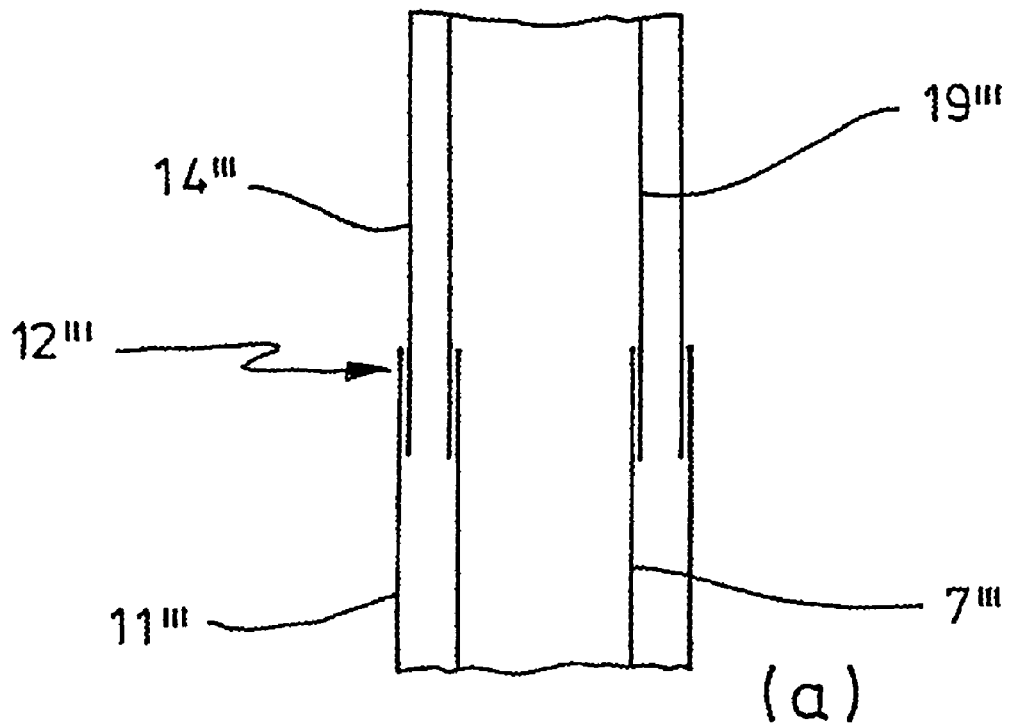
Figure 5:
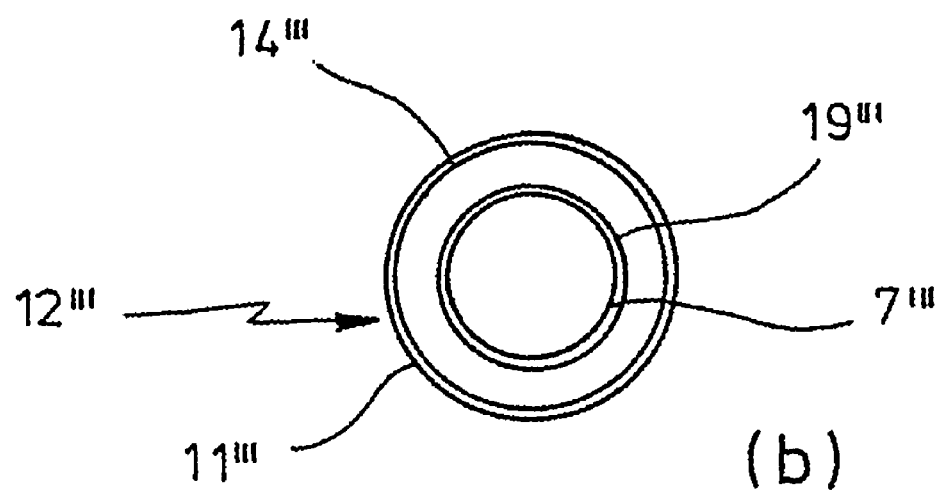

The embodiment in FIG. 5 differs from the ones described above by the cylindrical shape of the connecting piece 11''' and opening 14''' in their region of contact. Furthermore the opening 14''' is inserted into the connecting piece 11'''. For this purpose the opening 14''' has an external diameter of approximately 22 mm, the connecting piece 11''' having a corresponding internal diameter.

Like in the embodiments described above the tube 7''' is introduced into the tube 19''', the two tubes 7''' and 19''' featuring a wider diameter of approximately 15 mm.

Preferably the interior lumen of the tubes 7''' and 19''' is used for expiration and the ring shaped exterior lumen between the tubes 7''' and 19''' on the one hand and connecting piece 11''' and opening 14''' on the other for inspiration.

The invention claimed is:

1. Device for ventilation comprising
a double lumen endotracheal tube with an inspiratory lumen and an expiratory lumen and with a connecting piece at the end distal to the patient, both lumina of the endotracheal tube extending into the connecting piece and separated within it by an axial partition wall,
an independent connector with separate inspiratory and expiratory tube nozzles extending from a first end of the connector and that intersect within the connector to form inspiratory and expiratory chambers that remain separated from each other by a connector partition wall that extends from within the connector to an opening at the opposing end of the connector, said opening being connectable to the connecting piece of the double lumen endotracheal tube such that the partition wall of the endotracheal tube and the connector partition wall join to form a seal, and
a ventilator that is suitably connected to one or both of the inspiratory and expiratory tube nozzles at the first end of the connector,
wherein the connector features a shutter bridging the two sides of the connector partition wall, or in which the connecting piece of the endotracheal tube features a shutter bridging the two sides of the axial partition wall.

2. Device according to claim 1, in which the endotracheal tube connecting piece features a circular external circumference and the connector opening features a corresponding internal circumference such that the connector opening is removably connectable to the endotracheal tube connecting piece.

3. Device according to claim 1, in which the endotracheal tube connecting piece and the connector opening are both conical or both cylindrical.

4. Device according to claim 1, in which the connector is Y-shaped or T-shaped.

5. Device according to claim 1, in which the axial partition wall and the connector partition wall meet bluntly for forming a seal.

6. Device according to claim 1, in which the endotracheal tube partition wall and the connector partition wall both have a plate shape.

7. Device according to claim 1, in which the connecting piece of the endotracheal tube or a tube-shaped partition wall located within the connecting piece of the endotracheal tube has an external diameter of approximately 15 mm and the connector opening or another tube-shaped partition wall located within the connector opening has an internal diameter of approximately 15 mm.

8. Device according to claim 1, in which one of the connecting piece of the endotracheal tube and the connector features at least one groove and the other has at least one corresponding projection, wherein the groove and the projection articulate when the connecting piece and the connector are joined.

9. Device according to claim 1, in which the device includes a closing element in or on the shutter, and wherein the closing element has a seat in the respective partition wall.

10. Device according to claim 9, in which the closing element has an operating element that is externally and manually operated.

11. Device according to claim 1, in which the shutter features an operating connection with a control component of the ventilator.

12. Device according to claim 1, in which the shutter features an operating connection with a pressure sensor in an inspiratory or expiratory limb of one or more of the endotracheal tube, the connector, and the ventilator.

13. Device according to claim 1, in which the shutter has a sensor for the position of the closing element featuring an operating connection to a control component of the ventilator.

14. Device according to claim 1, in which the inspiratory and expiratory tube nozzles of the connector are attached to tubes that features joints which can be swiveled around at least one axis.

15. Device according to claim 1, in which the connector has a closable opening in the expiratory tube nozzle which, when opened, allows access into the expiratory lumen of the endotracheal tube.

16. Device according to claim 15, featuring a plug that, when introduced into the closable opening, forms a seal with the closable opening.

17. Device according to claim 15, in which the closable opening includes an elastic perforated membrane.

18. Device according to claim 1, in which the endotracheal tube partition wall and the connector partition wall partially overlap for forming a seal.

19. Device according to claim 1, in which the endotracheal tube partition wall and the connector partition wall both have a tube shape.

20. Device according to claim 1, in which the connecting piece of the endotracheal tube has an internal diameter of approximately 22 mm and the connector opening has an external diameter of approximately 22 mm.

21. A connector device for safely connecting an endotracheal tube to a further device, the connector comprising separate inspiratory and expiratory tube nozzles extending from a first end of the connector and that intersect within the connector to form inspiratory and expiratory chambers that remain separated from each other by a connector partition wall that extends from within the connector to an opening at the opposing end of the connector, said opening being connectable to an endotracheal tube such that, when the endotracheal tube is a double lumen endotracheal tube with a partition wall delineating the two lumina, such partition wall joins to the connector partition wall to form a seal, wherein the connector partition wall further comprises a shutter with a valve seat bridging the two sides of the connector partition wall to allow or disallow a fluid connection between the inspiratory and expiratory chambers in the connector.

22. Connector device according to claim 21, further comprising an operating element that is externally operated to open the shutter and allow a fluid connection between the inspiratory and expiratory chambers in the connector.

23. Connector device according to claim 22, wherein the operating element is manually operated.

24. Connector device according to claim 23, wherein the operating element is automatically operated.

25. Connector device according to claim 21, wherein the shutter comprises an operating connection with a control component of a ventilator to which the connector device can be attached.

26. Connector device according to claim 21, wherein the shutter comprises an operating connection with a pressure sensor in an inspiratory or expiratory limb of one or more of the connector, the endotracheal tube, and a ventilator to which the connector can be attached.

27. Connector device according to claim 21, wherein the shutter comprises a sensor for sensing whether the shutter is in an open or closed position.

28. Connector device according to claim 27, wherein the sensor is in an operating connection to a control component of a ventilator to which the connector can be attached.

29. Connector device according to claim 21, wherein the connector has a closable opening in the expiratory tube nozzle which, when opened, allows access into the expiratory lumen of the endotracheal tube.

30. Connector device according to claim 29, further comprising a plug that, when introduced into the opening, forms a seal with the opening.

31. Connector device according to claim 29, wherein the opening is sealed with an elastic membrane.

32. Connector device according to claim 21, wherein the connector is Y-shaped or T-shaped.

33. Connector device according to claim 21, wherein the separate inspiratory and expiratory chambers within the connector have a side-by-side configuration.

34. Connector device according to claim 21, wherein the separate inspiratory and expiratory chambers within the connector are a tube within a tube.

35. Connector device according to claim 21, wherein the connector comprises at least one groove or projection that articulates with a corresponding projection or groove on the endotracheal tube when the connector device is connected to the endotracheal tube.

36. A method of safely ventilating a patient with a double lumen endotracheal tube so as to provide for breathing of ambient air by the patient in cases of malfunction jeopardizing regular delivery of gas to the patient, said method comprising connecting a double lumen endotracheal tube for securing the airway of the patient to a ventilator or anesthesia machine via a connector device according to claim 21.

* * * * *